US009282987B2

(12) United States Patent
Jimenez

(10) Patent No.: US 9,282,987 B2
(45) Date of Patent: Mar. 15, 2016

(54) ORAL CARE IMPLEMENT

(75) Inventor: Eduardo J. Jimenez, Manalapan, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 46 days.

(21) Appl. No.: 13/982,459

(22) PCT Filed: Feb. 1, 2011

(86) PCT No.: PCT/US2011/023356
§ 371 (c)(1),
(2), (4) Date: Jul. 29, 2013

(87) PCT Pub. No.: WO2012/118472
PCT Pub. Date: Sep. 7, 2012

(65) Prior Publication Data
US 2013/0310860 A1 Nov. 21, 2013

(51) Int. Cl.
| A61B 17/24 | (2006.01) |
| A61C 15/04 | (2006.01) |
| A46B 15/00 | (2006.01) |
| A46B 5/02 | (2006.01) |

(52) U.S. Cl.
CPC ............ *A61B 17/244* (2013.01); *A46B 5/021* (2013.01); *A46B 15/0081* (2013.01); *A61C 15/046* (2013.01)

(58) Field of Classification Search
CPC ...... A61C 17/00; A61C 15/046; A61B 17/24; A61B 17/244
USPC ............. 606/161; 15/111, 143.1, 167.2, 172, 15/105, 167.1, 188, 104.94, 110, 201, 222, 15/233; 132/309, 323; 241/169.2, 168, 241/169.1; 30/279.4
See application file for complete search history.

(56) References Cited

U.S. PATENT DOCUMENTS

| 1,892,068 A | * | 12/1932 | Metzler .................... 601/139 |
| 5,984,935 A | * | 11/1999 | Welt et al. ................. 606/161 |
| 6,056,763 A | * | 5/2000 | Parsons .................... 606/161 |
| 6,083,235 A | * | 7/2000 | Wagner .................... 606/161 |
| 6,092,536 A | * | 7/2000 | Owens ...................... 132/325 |
| 6,625,839 B2 | * | 9/2003 | Fischer et al. .............. 15/160 |

(Continued)

FOREIGN PATENT DOCUMENTS

| CN | 2744315 | 12/2005 |
| CN | 201055404 | 5/2008 |

(Continued)

OTHER PUBLICATIONS

International Search Report and Written Opinion of the International Searching Authority in International Application No. PCT/US2011/023356 mailed Oct. 21, 2011.

(Continued)

*Primary Examiner* — Todd E Manahan
*Assistant Examiner* — Majid Jamialahmadi

(57) ABSTRACT

An oral care implement for cleaning soft oral tissue. In one aspect, the invention can be an oral care implement comprising: a handle extending along a longitudinal axis; first and second prong members extending from a distal end of the handle; a pad for engaging soft tissue, the pad having a first major surface and a second major surface, the pad positioned between and coupled to the first and second prong members.

16 Claims, 3 Drawing Sheets

(56) References Cited

U.S. PATENT DOCUMENTS

| | | |
|---|---|---|
| 7,090,687 B1 | 8/2006 | Gwen |
| 7,273,327 B2 | 9/2007 | Hohlbein et al. |
| 7,607,189 B2 | 10/2009 | Moskovich |
| 7,721,376 B2 | 5/2010 | Hohlein et al. |
| 2004/0092981 A1 | 5/2004 | Barlow et al. |
| 2005/0069372 A1 | 3/2005 | Hohlbein |
| 2006/0052805 A1* | 3/2006 | Cwik .......................... 606/161 |
| 2006/0052806 A1* | 3/2006 | Xi et al. ...................... 606/161 |
| 2006/0058821 A1* | 3/2006 | Jansheski .................... 606/161 |
| 2007/0166430 A1 | 7/2007 | Stawski et al. |
| 2008/0208228 A1 | 8/2008 | Mueller |
| 2009/0236454 A1* | 9/2009 | Schmidt .................... 241/169.2 |
| 2009/0308962 A1* | 12/2009 | Chapman et al. ......... 241/169.2 |

FOREIGN PATENT DOCUMENTS

| | | | |
|---|---|---|---|
| CN | 201668454 | 12/2010 | |
| JP | WO 01/00103 | * 4/2001 | ............ A61C 17/00 |
| NL | 2002311 | 6/2010 | |
| WO | WO01/00103 | 1/2001 | |
| WO | WO02/071967 | 9/2002 | |

OTHER PUBLICATIONS

Written Opinion of the International Preliminary Examining Authority in International Application No. PCT/US2011/023356 mailed Jan. 28, 2013.

* cited by examiner

ORAL CARE IMPLEMENT

CROSS-REFERENCE TO RELATED PATENT APPLICATIONS

The present application is a U.S. national stage application under 35 U.S.C. §371 of PCT Application No. PCT/US2011/023356, filed Feb. 1, 2011, the entirety of which is incorporated herein by reference.

FIELD OF THE INVENTION

The present invention relates generally to the field of oral care, and specifically to an apparatus for cleaning oral soft tissue, such as the tongue.

BACKGROUND OF THE INVENTION

According to the American Dental Association, a major source of bad breath in healthy people is microbial deposits on the tongue, where a bacterial coating harbors organisms and debris that contribute to bad breath. The tongue is a haven for the growth of microorganisms since the papillary nature of the tongue surface creates a unique ecological site that provides an extremely large surface area, favoring the accumulation of oral bacteria. Anaerobic flora and bacteria residing on the tongue play an important role in the development of chronic bad breath commonly called halitosis. In general, the bacteria produce volatile sulfur compounds (VSC). If there is enough buildup of the sulfur compounds, the result can be bad breath or oral malodor.

While bladed tongue scrapers have been used in the past in order to remove bacteria from the tongue, these scrapers are inadequate in respect to their effectiveness on the soft tissue surface of the tongue. Broad flat scraping blades are limited in their ability to reach between the papillae where the bacteria and microdebris have collected. Moreover, notwithstanding the benefits to be gained by any ability to clean the tongue, some users avoid the use of such blades because of lack of comfort on the tongue surface.

In addition to bladed tongue scrapers, toothbrushes have been developed that have a tissue cleanser on the toothbrush head. However, these oral care implements are limited in that the tissue cleanser is provided only on one major surface of the head.

Furthermore, known tongue scrapers and soft tissue cleansers have a predetermined width. Thus, for persons with small mouths, such as children, these known devices are inefficient or uncomfortable to use. While a tongue scraper having an adjustable width is known, such adjustable width tongue scrapers are both cumbersome and complicated in their manufacture and use, thereby resulting in the devices being expensive to manufacture and/or undesirable to use.

Hence, there is a need for an apparatus for cleaning soft tissue within a user's mouth that provides effective removal of bacteria and other debris while maintaining comfort to the user. There is also a need for an apparatus for cleaning soft tissue within a user's mouth in which a size of the portion of the apparatus that contacts the user's soft tissue is adjustable. There is a further need for an apparatus for cleaning soft tissue within a user's mouth which is easy to manufacture and has user-friendly design.

BRIEF SUMMARY OF THE INVENTION

The present invention is directed to an oral care implement for cleaning a user's soft oral tissue. The oral care implement comprises a handle and prong members extending from the handle. A pad for engaging the soft tissue is positioned between and secured to the prong members.

In one aspect, the invention can be an oral care implement comprising: a handle extending along a longitudinal axis; first and second prong members extending from a distal end of the handle, each of the first and second prong members diverging from the longitudinal axis; a pad for engaging soft tissue, the pad having a first major surface and a second major surface, the pad positioned between and coupled to the first and second prong members; and a plurality of protuberances protruding from the first major surface of the pad.

In another aspect, the invention can be an oral care implement comprising: a handle extending along a longitudinal axis; first and second prong members extending from a distal end of the handle; a pad for engaging soft tissue, the pad having a first major surface and a second major surface, the pad positioned between and coupled to the first and second prong members at an axial location; and wherein the first and second prong members are adjustable between (1) a normal state having a first distance between the first and second prong members at the axial location; and (2) a flexed state having a second distance between the first and second prong members at the axial location, wherein the second distance is less than the first distance, thereby bowing the pad.

In yet another aspect, the invention can be an oral care implement comprising: a handle extending along a longitudinal axis; first and second prong members extending from a distal end of the handle; a pad for engaging soft tissue, the pad having a first major surface and a second major surface, the pad positioned between and coupled to the first and second prong members; and wherein the pad comprises a base formed of a first material and a layer formed of a second material overlying at least a portion of the base, the first material having a hardness that is greater than a hardness of the second material.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

Figure 1:
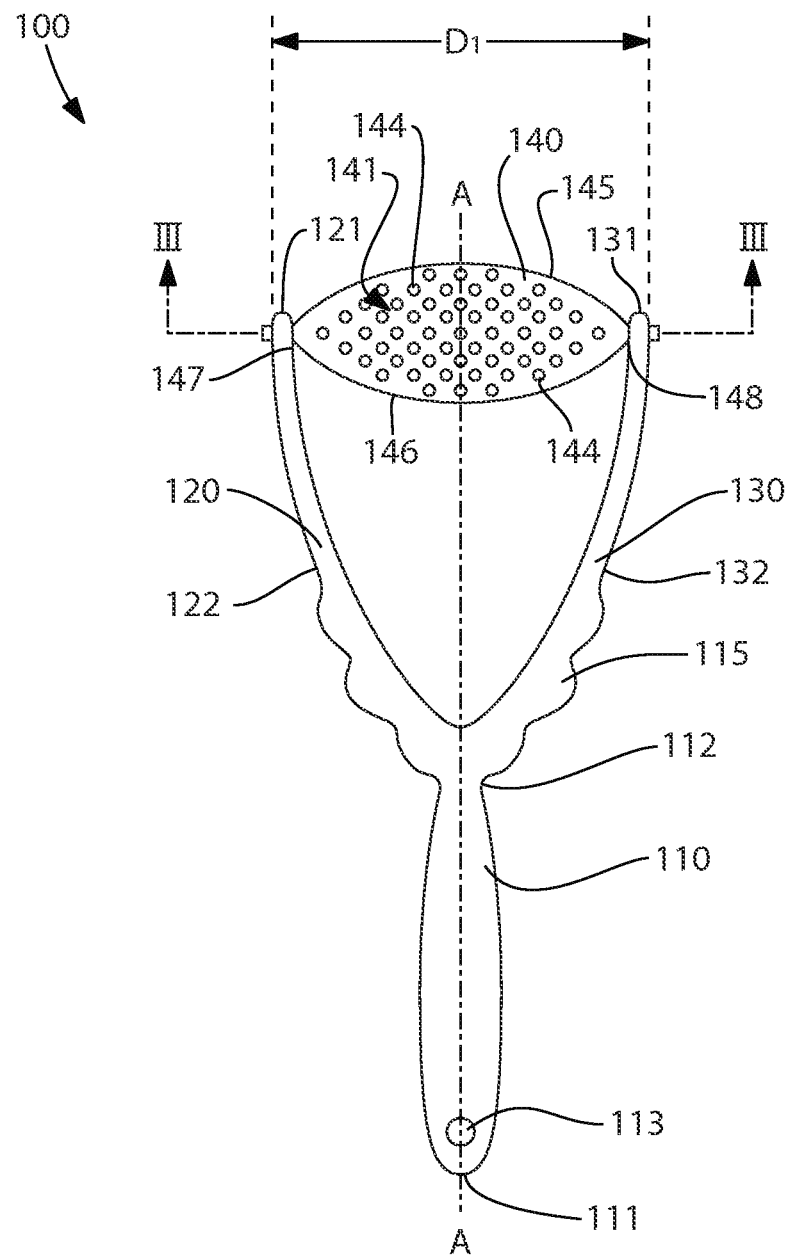
FIG. 1 is a front view of an oral care implement in a normal state in accordance with one embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of the exemplary embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "left," "right," "top," "bottom," "front" and "rear" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," "secured" and similar refer to a relationship wherein structures are secured or attached to one another either directly or indirectly through intervening structures, as well as both movable or rigid attachments or relationships, unless expressly described otherwise. Moreover, the features and benefits of the invention are described by reference to the exemplary embodiments illustrated herein. Accordingly, the invention expressly should not be limited to such exemplary embodiments, even if indicated as being preferred. The discussion herein describes and illustrates some possible non-limiting combinations of features that may exist alone or in other combinations of features. The scope of the invention is defined by the claims appended hereto.

Referring to FIG. 1, an oral care implement 100 is illustrated according to one embodiment of the present invention. The oral care implement generally comprises a handle 110, a first prong member 120, a second prong member 130 and a pad 140. The handle 110 provides a user with a mechanism by which he/she can readily grip and manipulate the oral care implement 100. The handle 110 may include ergonomic features which provide a high degree of control for the user during periods of use.

The handle 110 extends from a proximal end 111 to a distal end 112 along a longitudinal axis A-A. The handle 110 comprises an aperture 113 near its proximal end 111 to enable the oral care implement 100 to be hung from a hook, a nail or any other protruding member or post that can be used to hang items. Of course, in certain embodiments, the aperture 113 may be omitted from the handle 110 if desired.

The first and second prong members 120, 130 extend from the distal end 112 of the handle 110 in a forked-manner. More specifically, the first and second prong members 120, 130 extend from the distal end 112 of the handle 110 in a forked-manner such that the first and second prong members 120, 130 diverge from the longitudinal axis A-A with distance from the distal end 112 of the handle 110. As a result, the further the distance from the distal end 112 of the handle 110, the larger the transverse distance between the first and second prong members 120, 130. While the first and second prong members 120, 130 diverge from the longitudinal axis A-A along their entire length in the exemplified embodiment, in certain other embodiments, the first and second prong members 120, 130 may diverge from the longitudinal axis A-A only for a portion of their length. In such embodiments, the first and second prong members 120, 130 may diverge from the longitudinal axis A-A for only a portion of their length from the distal end 112 of the handle 110 and then: (1) straighten out and continue in a substantially parallel manner for their remainder; and/or (2) begin to converge toward the longitudinal axis A-A for their remainder.

In one embodiment, the handle 110 and the first and second prong members 120, 130 may be integrally formed as a unitary structure. In such an embodiment, the handle 110 transitions directly into the first and second prong members 120, 130 at the distal end 112 of the handle 110. Thus, the handle 110 and the first and second prong members 120, 130 will be a single-component formed of a hard, yet flexible material, such as a thermoplastic. In one specific embodiment, the handle 110 and the first and second prong members 120, 130 are integrally formed of polypropylene. Of course, the invention is not so limited and the handle 110 and the first and second prong members 120, 130 may be formed of other suitable materials. Moreover, in other embodiments, the handle 110 and the first and second prong members 120, 130 may be formed as separate components that are coupled at a later stage of the manufacturing process by any suitable technique known in the art, including without limitation thermal welding, a tight-fit assembly, threaded engagement, a coupling sleeve, adhesion, fasteners and/or combination thereof. Whether the handle 110 and the first and second prong members 120, 130 are of a unitary or multi-piece construction (including connection techniques) is not limiting of the present invention unless specifically recited.

In certain embodiments, the handle 110 and the first and second prong members 120, 130 may include an overlay that covers a portion of each of the handle 110, the first prong member 120, and/or the second prong member 130. In certain embodiment, the overlay may be formed of a resilient material, such as, for example, a thermoplastic elastomer. Thus in one embodiment, a core (or base) of the handle 110, the first prong member 120, and/or the second prong member 130 may be formed of a hard, yet flexible, plastic that is covered with a softer resilient material. Such an assembly may provide for easy gripping, flexing and squeezing of the prong member 120, 130, as will be discussed in more detail below with reference to FIG. 4.

The prong members 120, 130 are provided with finger grip protrusions 115. The finger grip protrusions 115 are a series of protuberances on outer surfaces 122, 132 of the first and second prong members 120, 130 that form an undulating surface. The finger grip protrusions 115 create a surface in which a user's fingers can nest during use. The finger grip protrusions 115 may be constructed of the resilient material if an overlay is used. In other embodiments, the finger grip protrusions 115 may be integrally formed into the hard plastic material, such as polypropylene. Of course, in certain other embodiments, the finger grip protrusions 115 may be omitted altogether.

It should be understood that as used herein, components are "integrally formed" when they form one undivided unitary structure, irrespective of the formation process. For example, components can be integrally formed using a molding, milling, machining or other suitable process.

The first prong member 120 terminates in a distal end 121 and includes an outer surface 122. Similarly, the second prong member 130 terminates in a distal end 131 and includes an outer surface 132. The pad 140 is positioned between and coupled to the first and second prong members 120, 130 in a manner that will be discussed below. In the illustrated embodiment, the pad 140 is coupled to the first and second prong members 120, 130 at or near the distal ends 121, 131 of the first and second prong members 120, 130. In the exemplified embodiment, the pad 140 extends axially beyond the distal/terminal ends 121, 131 of the first and second prong member 120, 130. More specifically, the edge 145 of the pad 140 extends axially beyond the distal/terminal ends 121, 131 of the first and second prong member 120, 130. Such an arrangement may be desirable in certain embodiments, as is allows the pad 140 to reach further into the oral cavity without being limited by the added width necessary to accommodate the prong members 120, 130. Of course, the invention is not so limited and the pad 140 may be secured to the first and second prong members 120, 130 at other axial locations if desired.

Figure 2:
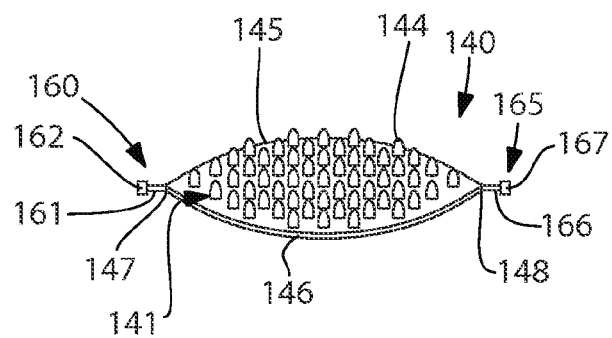
FIG. 2 is a perspective view of the pad of the oral care implement of FIG. 1 removed from the handle and prong structure, the pad being in a substantially flat state in accordance with one embodiment of the present invention.
Figure 3:
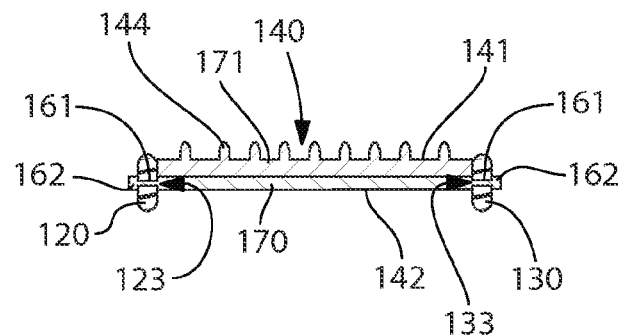
FIG. 3 is a transverse cross-sectional view taken along line III-III of FIG. 1.

Referring now to FIGS. 2 and 3 concurrently, an embodiment of the pad 140 will be described in more detail. The pad 140 has a first major surface 141 and a second major surface 142 opposite the first major surface 141. The first major surface 141 of the pad 140 is the portion of the pad 140 that engages a user's soft oral tissue during use of the oral care implement 100. In certain embodiments, the second major surface 142 of the pad 140 may also be configured to engage a user's soft tissue surfaces. In such embodiments, the first major surface 141 of the pad 140 may be formed of a first soft material having protuberances for engaging the soft oral tissue and the second major surface 142 of the pad 140 may be formed of a harder material having protuberances for engaging the soft oral tissue. Moreover, in another embodiment, both the first and second major surfaces 141, 142 of the pad 140 may include protuberances forming different topographies, irrespective of whether the first and second major surfaces 141, 142 of the pad 140 are formed of the same or different materials. In one such embodiment, the protuberances of the first major surface 141 of the pad 140 are nubs while the protuberances on the second major surface 142 of the pad 140 may be transversely extending ridges.

In the exemplified embodiment, the pad 140 is a plate-like structure, As a result, the first and second major surfaces 141, 142 are substantially parallel to one another. Furthermore, in the exemplified embodiment, the pad 140 has an elliptical or elongated ovoid shape. However, the invention is not so limited and the pad 140 may take on other shapes including, without limitation, rectangular, circular, triangular or any other irregular or polygonal shape as desired.

A plurality of protuberances 144 are provided on and protrude from the first major surface 141 of the pad 140. The plurality of protuberances 144 are intended to engage the soft oral tissue of a user's mouth, such as the tongue, in order to provide an effective and efficient cleaning. Specifically, when the first major surface 141 of the pad 140 is engaged or otherwise pulled against or across the desired soft oral tissue, such as the tongue, the protuberances 144 will penetrate and engage the soft oral tissue while reaching downward into the recesses, crevices and/or pockets of the soft oral tissue.

In the exemplified embodiment, the plurality of protuberances 144 are provided in axial rows wherein adjacent axial rows are staggered. It should be understood that the number and arrangement of protuberances 144 on the first major surface 141 of the pad 140 are in no way limiting of the present invention. Thus, in certain embodiments the first major surface 141 of the pad 140 comprises a single axial row of tightly packed protuberances 144. Furthermore, in other embodiments, the protuberances 144 can be arranged in rows that are aligned rather than staggered. In still other embodiments, the protuberances 144 can be arranged irregularly.

In some embodiments, the plurality of protuberances 144 are formed as nubs. As used herein, the term "nub" is generally meant to include a column-like protrusion (without limitation to the cross-sectional shape of the protrusion) which is upstanding from a base surface, such as the first major surface 141 of the oral care implement 100. In a general sense, the nub, in one construction, has a height that is greater than the width at the base of the nub (as measured in the longest direction). Nevertheless, nubs could include projections wherein the widths and heights are roughly the same or wherein the heights are somewhat smaller than the base widths.

Moreover, in some circumstances (e.g., where the nub tapers to a tip as illustrated in FIG. 2 or where the nub includes a base portion that narrows to a smaller projection), the base width can be substantially larger than the height. Of course, the protuberances 144 are not limited to column-like or cylindrical nubs, and the protuberances 144 can take on a wide variety of shapes and structures, including conical, rod-like, hemi-spherical, irregular or the like.

Furthermore, in other embodiments, the protuberances 144 can take on other shapes, such as ridges. In still other embodiments, the protuberances 144 on the first major surface 141 can be a combination of ridges and nubs. As mentioned above, the protuberances 144 can be added to the second major surface 142 of the pad 140 if desired.

The pad 140 further comprises a top edge 145, a bottom edge 146, and first and second side edges 147, 148. The top and bottom edges 145, 146 converge towards each other and meet at each of the side edges 147, 148. A first tang 160 transversely extends from the first side edge 147 of the pad 140 and a second tang 165 transversely extends from the second side edge 148 of the pad 140, in a direction opposite the first tang 160. The first tang 160 includes a first post member 161 and a first annular flange 162 while the second tang 165 includes a second post member 166 and a second annular flange 167.

A proximal end of the first post member 161 is connected to the first side edge 147 of the pad 140 while the first annular flange 162 is located at the distal end of the first post member 161. Similarly, a proximal end of the second post member 166 is connected to the second side edge 148 of the pad 140 while the second annular flange 167 is located at the distal end of the second post member 165. The first and second post members 161, 166 are rod-like structures that extend from the first and second side edges 147, 148 of the pad 140 respectively. In the exemplified embodiment, the first and second post members 161, 166 and the first and second annular flanges 162, 167 are used to couple the pad 140 to the first and second prong members 120, 130, as will be described in greater detail below.

A first aperture 123 extends through the first prong member 120 at or near the distal end 121 of the first prong member 120. Similarly, a second aperture 133 extends through the second prong member 130 at or near the distal end 131 of the second prong member 130. The openings of the first and second apertures 123, 133 are sized to receive the first and second post members 161, 166 therein while preventing the first and second annular flanges 162, 167 from passing therethrough. In other words, the transverse cross-sectional areas of the first and second post members 161, 166 correspond to the transverse cross-sectional areas of the apertures 123, 133 (with of course a desired tolerance) to enable the post members 161, 166 to fit within the apertures 123, 133. To the contrary, the first and second annular flanges 162, 167 have transverse cross-sectional areas that are larger than the transverse cross-sectional areas of the first and second apertures 123, 133. Thus, the first and second annular flanges 162, 167 are unable to slide through the apertures 123, 133. This allows the pad 140 to be coupled to the first and second prong members 120, 130.

When the pad 140 is secured to the first and second prong members 120, 130, the first post member 161 is positioned within the first aperture 123 and the second post member 166 is positioned within the second aperture 133. The first annular flange 162 is positioned outside of the first aperture 123 and abuts against the outer surface 122 of the first prong member 120. Similarly, the second annular flange 167 is positioned outside of the second aperture 133 and abuts against the outer surface 132 of the second prong member 130.

In the exemplified embodiment, two tangs 160, 165 are illustrated to secure the ovoid-shaped pad 140 to the first and second prong members 120, 130. However, in alternate embodiments, more than two tangs may be used. For example, when the pad 140 is rectangular-shaped, four or more tangs may be used to secure the pad 140 to the first and second prong members 120, 130. The number of tangs used to secure the pad 140 to the first and second prong members 120, 130 is dependent upon the shape of the pad 140, the desired use of the pad 140, and the number of degrees of freedom desired between the pad 140 and the first and second prong member 120, 130.

In the exemplified embodiment, the pad 140 is pivotably secured to the first and second prong members 120, 130. The attachment between the tangs 160, 165 and the first and second prong members 120, 130 enables the pad 140 to have 360° rotation about an axis that is perpendicular to the longitudinal axis A-A. The rotatability of the pad 140 relative to the prong member 120, 130 enables the pad 140 to reach different areas of the oral cavity and the soft oral tissue surfaces by allowing alteration of the angle of engagement through rotation. However, the invention is not so limited in all embodiments. In certain embodiments, the pad 140 will be unable to move or rotate relative to the first and second prong members 120, 130.

Furthermore, although the invention is described wherein the first and second annular flanges 162, 167 are unable to fit through the apertures 123, 133, in certain embodiments the pad 140 is intended to be removable and replaceable. In such embodiments, the first and second annular flanges 162, 167 can be designed to have a tolerance so that upon appropriate force being applied, the first and second annular flanges 162, 167 will pass through the apertures 123, 133. The force should be much greater than that which is experience during normal oral care routines to prevent accidental separation during oral care use. In other embodiments where the pad 140 is removable and replaceable from the prong member 120, 130, other structures and structural cooperation can be utilized to achieve the goal. For example, cotter pins, threaded connections, snap-fit connection, and/or interference fits can be used.

In one example, to effectuate removability and replaceability, the apertures 123, 133 may be formed as open end slots formed into the distal ends 121, 131 of the first and second prong members 120, 130. In such an embodiment, the first and second post members 161, 166 can slide into and out of the open end of the slots 123, 133 for insertion or removal of the pad 140. A suitable structure can be used to lock the pad 140 in place after slidable insertion. In another embodiment, the first and second annular flanges 162, 167 can be separable from the first and second post members 161, 166, respectively. For example, the first and second annular flanges 162, 167 can be threaded screw members that are capable of being detached from the first and second post members 161, 167.

Referring solely now to FIG. 3, the construction of the pad 140 according to one embodiment of the invention will be described in greater detail. The pad 140 is comprised of a base 170 formed of a first material and a layer 171 formed of a second material. The layer 171 overlies at least a portion of the base 170 to provide comfortable and efficient cleaning of the soft tissue surfaces. In alternate embodiments, the pad 140 can be formed of a single material, either the first material or second material, and/or as a single layer if desired.

In the exemplified embodiment, the first and second tangs 160, 165 are formed integrally with the base 170 of the pad 140 to provide a secure coupling between the pad 140 and the first and second prong members 120, 130. Of course, the invention is not so limited and the tangs 160, 165 may be formed integrally with the layer 171 of the pad 140 in certain embodiments. In certain other embodiments, the tangs 160, 165 may be components that are manufactured separately from the pad 140 and are later attached to the pad 140 by any suitable technique known in the art, including without limitation thermal welding, a tight-fit assembly, a coupling sleeve, adhesion, fasteners or the like.

The first material has a hardness value that is greater than a hardness value of the second material. In one embodiment, the first material has a hardness value in a range of 80 to 100 Shore A and the second material has a hardness value of approximately 30 to 50 Shore A. In one more specific embodiment, the material has a hardness value of approximately 90 Shore A and the second material has a hardness value of approximately 40 Shore A. In one specific embodiment, the base 170 is constructed of hard plastic, such as polypropylene, and the layer 171 is formed of a resilient material such as, for example, an elastomer. Of course, the invention is not so limited and other suitable materials may be used for the base 170 and the layer 171.

In certain embodiments, the pad 140 can be integrally formed with the first and second prong members 120, 130. In one such embodiment, the base 170 of the pad 140 can be integrally formed with the first and second prong members 120, 130 and then later covered with the layer 171. Of course, in certain other embodiments, the layer 171 may be omitted altogether. When integrally formed, the pad 140 is non-rotatable with respect to the prong member 120, 130. Having a non-rotatable pad 140 may enable deeper penetration of the protuberances 144 because the pad 140 is more stable than when the pad 140 is rotatable.

The base 170 provides a certain degree of rigidity to the pad 140, which makes the pad 140 more effective during use. Specifically, the base 170 provides sufficient rigidity to enhance penetration of the protuberances 144 while also enabling the pad 140 to bend and bow to fit the contours of the soft oral tissue surfaces, as will be described in detail below.

In the exemplified embodiment, the plurality of protuberances 144 are integrally formed with the layer 171 and, thus, the protuberances 144 are constructed of the same material as the layer 171. In such an embodiment, when the layer 171 is a soft resilient material, the protuberances 144 are also formed of the soft resilient material.

The layer 171 forms the first major surface 141 of the pad 140 in the exemplified embodiment. Thus, the first major surface 141 of the pad 140 and the protuberances 144 extending therefrom, which are the portions of the pad 140 that contact and engage the soft oral tissue, are formed of a soft resilient material. The soft resilient material of the layer 171 enables the first major surface 141 of the pad 140 to more closely follow the natural contours of the soft oral tissue, such as the tongue, cheeks, lips, and gums of a user. Moreover, the soft resilient material of the protuberances 144 enables the protuberances 144 to flex as needed to penetrate and clean the soft oral tissue when the oral care implement 100 is used.

As mentioned above, the layer 171 may be omitted altogether in certain alternate embodiments. In such an embodiment, the protuberances 144 can be formed directly on and/or from the material of the base 170. In such embodiments, the protuberances 144 will be formed of the harder material of the base 170. Forming the protuberances 144 of the harder base material may provide a more rigid cleaning surface of the pad 140 for an abrasive and thorough cleaning of the soft tissue surfaces.

Referring to FIGS. 1, 3, 4 and 5 concurrently, the adjustability of the width of the oral care implement 100 will be described. FIGS. 1 and 3 illustrate the oral care implement 100 in the normal state. In the normal state, there are no transverse forces or pressures being applied to the first and second prong members 120, 130 and the oral care implement 100 is in its natural shape. When in the normal state, the first and second major surfaces 141, 142 of the pad 140 are substantially planar surfaces.

The pad 140 is secured to the first and second prong members 120, 130 at an axial location as discussed above. As used herein, the axial location is the location of the point of attachment between the pad 140 and the first and second prong members 120, 130 as measured along the longitudinal axis A-A. In the normal state, there is a first distance $D_1$ between the outer surface 122 of the first prong member 120 and the outer surface 132 of the second prong member 130 at a first axial location.

Figure 5:
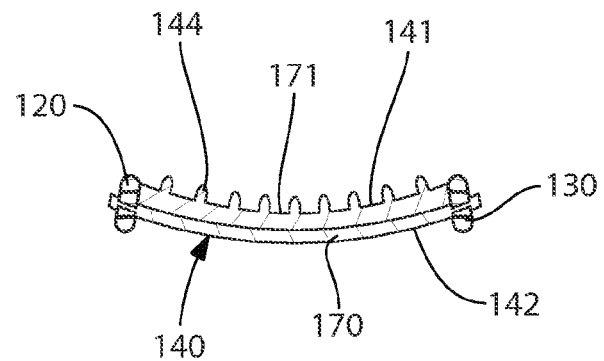
FIG. 5 is a transverse cross-sectional view taken along the line V-V of FIG. 4.
Figure 4:
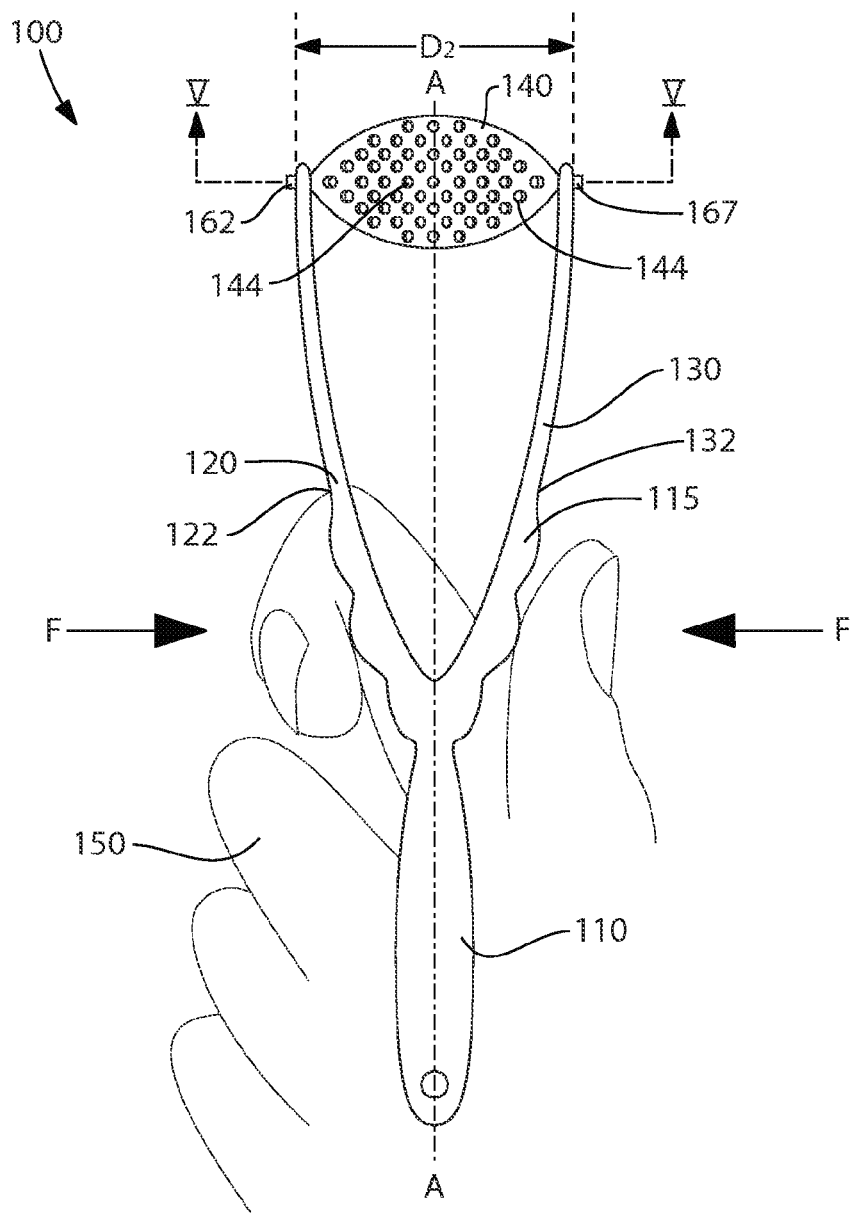
FIG. 4 is a front view of the oral care implement of FIG. 1 in a flexed state.

FIGS. 4 and 5 illustrate the oral care implement 100 in a flexed state. The oral care implement 100 is adjusted from the normal state to the flexed state by applying a force F to the outer surfaces 122, 132 of the first and second prong members 120, 130, such as by applying pressure to the finger grip protrusions 115. In the illustrated embodiment, the force F is created by a user's hand 150 squeezing the outer surfaces 122, 132 of the first and second prong members 120, 130 at the finger grip protrusions 115 in an inward direction as shown by the arrows. Of course, the invention is not so limited and the force F may be applied in other ways.

The force F is applied to the outer surfaces 122, 132 of the first and second prong members 120, 130 in a direction generally perpendicular to the longitudinal axis A-A. In the fully flexed state, illustrated in FIG. 4, there is a second distance $D_2$ between the outer surface 122 of the first prong member 120 and the outer surface 132 of the second prong member 130 at the first axial location. The second distance $D_2$ is less than the first distance $D_1$, such that the first and second prong members 120, 130 are closer to each other in the flexed state than in the normal state.

While FIG. 4 illustrates the oral care implement 100 in a fully flexed state, the oral care implement 100 may be flexed to less than the fully flexed state. Specifically, the greater the force F that acts on the outer surfaces 122, 132 of the first and second prong members 120, 130, the closer together the first and second prong members 120, 130 will become. A smaller force will press the first and second prong members 120, 130 together, but to a lesser extent. In other words, the second distance $D_2$ decreases as the force F increases.

As the force F is applied to the first and second prong members 120, 130 and the distance between the first and second prong members 120, 130 at the first axial location changes from $D_1$ to $D_2$ or any distance therebetween, the pad 140 bows or curves. In the exemplified embodiment, as the force F is applied to the outer surfaces 122, 132 of the first and second prong members 120, 130, the pad 140 bows so that the first major surface 141 of the pad 140 becomes concave (FIG. 5) to enable the pad 140 to fit the contours of a user's tongue or soft tissue surfaces. Of course, the invention is not so limited and in certain embodiments the pad 140 bows so that the first major surface 141 of the pad 140 is convex to provide deeper penetration of the protuberances into a user's soft tissue surfaces. Whether the pad 140 bows so that the first major surface 141 of the pad 140 becomes concave or convex in the flexed state can be controlled by the user applying a pre-force to one the first or second major surfaces 141, 142 as desired to effectuate the desired direction of bowing.

As soon as the force F is terminated, the first and second prong members 120, 130 are biased back to the normal state illustrated in FIG. 1. In other words, the first and second prong members 120, 130 remain in the normal state unless a force F is applied to the outer surfaces 122, 132 of the first and second prong members 120, 130. Furthermore, the first and second prong members 120, 130 return to the normal state automatically when the force F is no longer applied, and the pad 140 returns to its substantially planar form accordingly.

While a number of embodiments of the current invention have been described and illustrated in detail, various alternatives and modifications will become readily apparent to those skilled in the art without departing from the spirit and scope of the invention. As various changes could be made in the above methods, compositions and structures without departing from the scope of the invention, it is intended that all matter contained in this application, including all mechanisms and/or modes of interaction described above, shall be interpreted as illustrative only and not limiting in any way the scope of the appended claims.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

What is claimed is:

1. An oral care implement comprising:
   a handle extending along a longitudinal axis;
   first and second prong members extending from a distal end of the handle;
   a pad for engaging soft tissue, the pad having a first major surface and a second major surface, the pad positioned between and coupled to the first and second prong members; and
   a plurality of protuberances protruding from the first major surface of the pad;
   wherein the pad is coupled to the first and second prong members at an axial location, and wherein the first and second prong members are adjustable between (1) a normal state having a first distance between the first and second prong members at the axial location; and (2) a flexed state having a second distance between the first and second prong members at the axial location, wherein the second distance is less than the first distance;
   wherein in the flexed state the pad is bowed by the first and second prong members; and
   wherein the pad is rotatably coupled to the first and second prong members for 360° rotation about a rotational axis.

2. The oral care implement of claim 1 wherein the pad comprises a base formed of a first material and a layer formed of a second material overlying at least a portion of the base, the first material having a hardness that is greater than a hardness of the second material, the plurality of protuberances integrally formed with the second material.

3. The oral care implement of claim 1 wherein the pad is adjusted from the normal state to the flexed state upon force being applied to an outer surface of each of the first and second prong members.

4. The oral care implement of claim 1 wherein the first major surface of the pad is planar in the normal state and concave in the flexed state.

5. The oral care implement of claim 1 wherein each of the first and second prong members further comprises a plurality of finger grip protrusions.

6. The oral care implement of claim 1 wherein the handle and the first and second prong members are integrally formed as a unitary structure.

7. The oral care implement of claim 1 wherein the rotational axis is perpendicular to the longitudinal axis.

8. An oral care implement comprising:
a handle extending along a longitudinal axis;
first and second prong members extending from a distal end of the handle; and
a pad for engaging soft tissue, the pad having a first major surface and a second major surface, the pad positioned between and coupled to the first and second prong members at an axial location;
wherein the first and second prong members are adjustable between (1) a normal state having a first distance between the first and second prong members at the axial location; and (2) a flexed state having a second distance between the first and second prong members at the axial location, wherein the second distance is less than the first distance; and
wherein the pad is substantially flat in the normal state and bowed in the flexed state; and
wherein the pad is rotatably coupled to the first and second prong members for 360° rotation about a rotational axis.

9. The oral care implement of claim 8 wherein the first and second prong members are biased into the normal state.

10. The oral care implement of claim 8 wherein the first and second prong members are adjusted into the flexed state by applying force to an outer surface of each of the first and second prong members.

11. The oral care implement of claim 8 further comprising a plurality of protuberances protruding from the first major surface of the pad.

12. The oral care implement of claim 8 wherein the rotational axis is perpendicular to the longitudinal axis.

13. An oral care implement comprising:
a handle extending along a longitudinal axis;
first and second prong members extending from a distal end of the handle; and
a pad for engaging soft tissue, the pad having a first major surface and a second major surface, a plurality of protuberances protruding from the first major surface of the pad, the pad positioned between and coupled to the first and second prong members;
wherein the pad comprises a base formed of a hard plastic material and a layer formed of a resilient material overlying at least a portion of the base, the hard plastic material having a hardness that is greater than a hardness of the resilient material;
wherein the pad is coupled to the first and second prong members at an axial location, and wherein the first and second prong members are adjustable between (1) a normal state having a first distance between the first and second prong members at the axial location; and (2) a flexed state having a second distance between the first and second prong members at the axial location, wherein the second distance is less than the first distance;
wherein the first major surface of the pad is formed of the resilient material and the second major surface of the pad is formed of the hard plastic material; and
wherein the pad is rotatably coupled to the first and second prong members for 360° rotation about a rotational axis.

14. The oral care implement of claim 13 wherein the hard plastic material is polypropylene and the resilient material is a thermoplastic elastomer.

15. The oral care implement of claim 13 wherein the rotational axis is perpendicular to the longitudinal axis.

16. The oral car eimplement of claim 13 wherein the protuebrances are formed of the resilient material.

* * * * *